(12) United States Patent
Dascalu

(10) Patent No.: US 7,452,556 B2
(45) Date of Patent: Nov. 18, 2008

(54) COMPOSITIONS FOR THE TREATMENT OF PILOSEBACEOUS GLAND INFLAMMATIONS COMPRISING ALUMINUM FLUORIDE

(75) Inventor: Avi Dascalu, Tel-Aviv (IL)

(73) Assignee: Medidermis Ltd. (IL)

( * ) Notice: Subject to any disclaimer, the term of this patent is extended or adjusted under 35 U.S.C. 154(b) by 497 days.

(21) Appl. No.: 10/490,600

(22) PCT Filed: Oct. 2, 2002

(86) PCT No.: PCT/IL02/00800

§ 371 (c)(1),
(2), (4) Date: Mar. 23, 2004

(87) PCT Pub. No.: WO03/028740

PCT Pub. Date: Apr. 10, 2003

(65) Prior Publication Data

US 2004/0202725 A1 Oct. 14, 2004

(30) Foreign Application Priority Data

Oct. 4, 2001 (IL) .................................... 145751

(51) Int. Cl.
*A61K 33/14* (2006.01)
*A61K 33/06* (2006.01)
*A61K 31/203* (2006.01)
*A61K 31/343* (2006.01)
*A61P 17/00* (2006.01)
*A61P 17/10* (2006.01)
*A61P 29/00* (2006.01)

(52) U.S. Cl. ................ 424/673; 424/613; 424/642; 424/682; 424/703; 424/713; 424/725; 514/159; 514/169; 514/464; 514/529; 514/530; 514/556; 514/557; 514/573; 514/703; 514/725; 514/734; 514/859; 514/887

(58) Field of Classification Search ............. 424/673, 424/613, 642, 73, 682, 703, 725; 514/159, 514/169, 464, 529, 530, 556, 557, 573, 703, 514/725, 734, 859, 887
See application file for complete search history.

(56) References Cited

U.S. PATENT DOCUMENTS

| 3,995,029 A | | 11/1976 | Weisz |
| 4,568,540 A | | 2/1986 | Asamo et al. |
| 4,943,432 A | * | 7/1990 | Biener ................ 424/647 |
| 5,549,885 A | * | 8/1996 | Torchinsky ............ 424/54 |
| 5,667,790 A | * | 9/1997 | Sellers, Jr. ............ 424/401 |
| 5,674,539 A | * | 10/1997 | Tomas ................ 424/702 |

FOREIGN PATENT DOCUMENTS

WO WO 98 24427 A 6/1998

OTHER PUBLICATIONS

National Psoriasis Foundation, www.psoriasis.org/about/faq/index.php, Dec. 21, 2006.*
Sigma Aldrich MSDS, Aluminum Fluoride, Apr. 10, 2006.*
Lai-Hao Wang and Shu-Jen Tsai, "Voltammetric behavior of chlorhexidine at a film mercury electrodes and its determination in cosmetics and oral hygiene products", Analytica Chimica Acta, 2001, 441: 107-116.*
Shelley, W.B. et al., Anhydrous Formulation Of Aluminum Chloride For Chronic Folliculitis, Jama: The Journal Of The American Medical Association, Oct. 24, 1980, pp. 1956-1957, vol. 244 No. 17.

* cited by examiner

*Primary Examiner*—John Pak
*Assistant Examiner*—Nathan W Schlientz
(74) *Attorney, Agent, or Firm*—Marianne Fuierer; Moore & Van Allen PLLC

(57) ABSTRACT

The present invention relates to compositions for the treatment of pilosebaceous gland inflammations, especially of the hair follicle and its appendages, in particular of Acne Vulgaris and Folliculitis, comprising as active ingredient AlF or chemical compounds which finally release AlF, or combinations of aluminum and fluoride salts which finally release AlF. AlF in accordance with the present invention relates to Aluminum fluoride (Aluminum Trifluoride; Aluminum Fluoride), CAS No 7784-18-1, EINECS No. 232-051-1, having an empirical formula of $AlF_3$. Said compositions have, inter alia, pharmaceutical, cosmetic or quasi-cosmetic properties. The present invention also relates to the use of said compositions in said treatment, and to methods for the treatment of pilosebaceous gland inflammations with said compositions.

13 Claims, 7 Drawing Sheets

Arrows represent reference points

Arrows represent reference points

Figures 0, 1A, 1B, 1C, 14, 26:
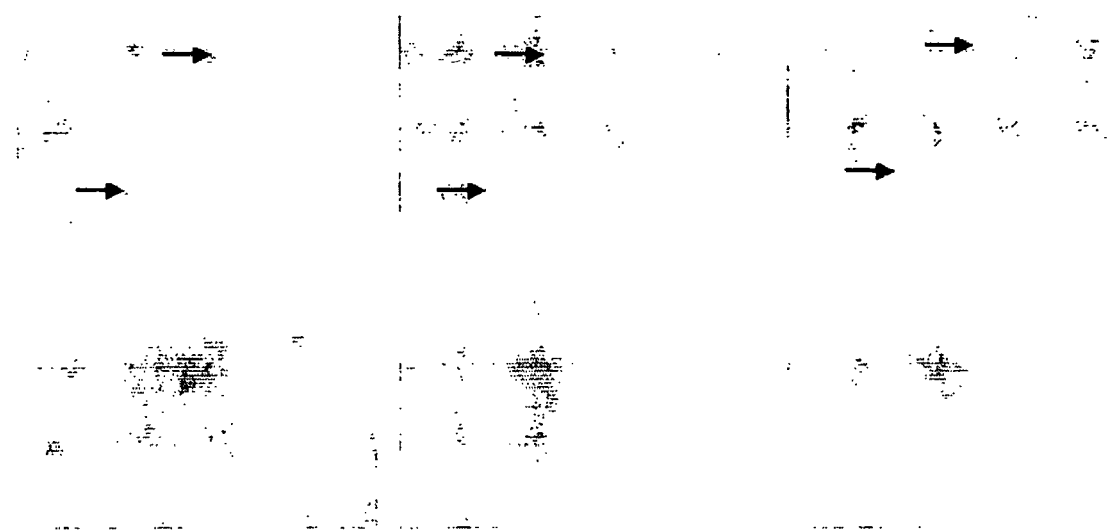

FIG. 5a
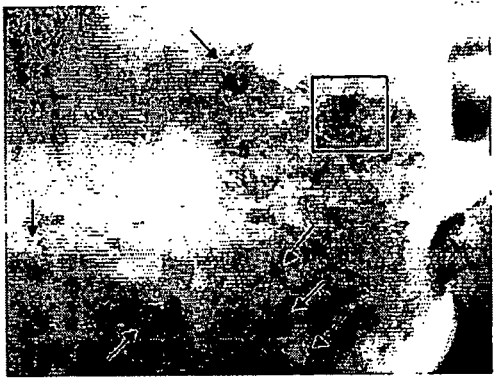
Severe Acne
Before treatment
FIG. 5c
4 Months Later
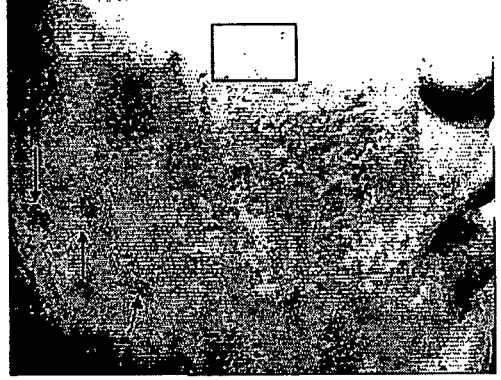
6 weeks from
start of treatment
FIG. 5b FIG. 6a
Before
Moderate Acne
After 3 months of treatment
FIG. 6b

COMPOSITIONS FOR THE TREATMENT OF PILOSEBACEOUS GLAND INFLAMMATIONS COMPRISING ALUMINUM FLUORIDE This application is a 371 of PCT/IL02/00800, filed on 2 Oct. 2002.

The present invention relates to compositions for the treatment of pilosebaceous gland inflammations, especially of the hair follicle and its appendages, in particular of Acne Vulgaris and Folliculitis. Said compositions have, inter alia, pharmaceutical, cosmetic or quasi-cosmetic properties. The present invention also relates to the use of said compositions in said treatment; and to methods for the treatment of pilosebaceous gland inflammations with said compositions.

The present invention will be illustrated herein in particular with reference to Acne Vulgaris and Folliculitis but is not restricted to these pilosebaceous gland inflammations.

The pathophysiology of Acne Vulgaris is multifactorial. It involves a genetic tendency of the hair infundibulum to narrow resulting in a keratin plug formation in the sebaceous gland ductuli. This is accompanied, in part of the subjects, by an androgenic-related sebum hypersecretion, causing noninflammatory lesions, i.e. closed and open comedos. Concomitantly, some of the lesions evolve into an inflammatory process, triggered in part by free fatty acids release into the dermis, together with a secondary microbial colonization of the pilosebaceous unit. The overall inflammatory and noninflammatory lesions are defined as Acne Vulgaris. The inflammatory lesions are responsible for the long lasting cosmetically disfiguring scars.

It has been amply described in the past (Fitzpatrick et al., Dermatology in Internal Medicine, McGraw Hill, In, 4th Edition, 1993) that Acne Vulgaris might be exacerbated by exposure to or intake of various chemicals and molecules, such as mechanical pressure, foods, drugs, halogens, tars, cosmetics and aluminum fluoride-containing toothpastes (Epstein E. Arch. Dermatol Fluoride toothpastes as a cause of acne-like eruptions, 1976 July, 112(7):10334). An inflammatory process is responsible for the classical clinical signs, such as papules (elevated palpable red areas) and pustules.

A process similar to inflammatory acne is Folliculitis, an "inflammation of a follicle or follicles." (Dorland's Illustrated Medical Dictionary, WB Saunders Comp., 27th Edition, 1988). It results from a microbial colonization and infection of the hair follicle shaft. Folliculitis is commonly accompanied by a perifollicular inflammation, perceived as classical inflammation signs of redness, swelling and tenderness at the basis of the hair shaft. More severe cases appear as significant perifollicular inflammation, named furuncle, carbuncles, impetigo, etc. The clinical picture of an inflammatory acne lesion and Folliculitis are identical, and Folliculitis is part of the acne pathophysiology. Mechanical trauma may induce or aggravate Folliculitis as well. However, a basic difference delineates these two entities: 1) The areas of distribution of the lesions in acne are seborrheic (e.g. face, chest, upper back), unlike Folliculitis, which manifests itself on seborrheic and non-seborrheic body areas and 2) Folliculitis is not related to genetic predisposition and hormonal changes.

From a practical point of view the treatment is alike: anti-inflammatories in conjunction with anti-microbials are started in mild cases as topicals. A more severe spread or degree of lesions require a combined systemic treatment. Agents which change the pilosebaceous unit function, such as retinoids, are sometimes used in Acne Vulgaris and stubborn Folliculitis (barbae). Control of Acne Vulgaris, specifically, requires the additional use of classical drugs, such as astringents, sulfur and benzoyl peroxide.

As will be detailed below, current treatment of Acne Vulgaris and Folliculitis is either largely ineffective or involves chronic systemic administration of drugs that cause numerous undesirable side-effects. Hence, it has been desired in the art to provide an effective and convincing treatment for both entities. A definitive highly efficacious, fast acting and low side effects solution is lacking. Various compositions are known in the art for controlling these pilosebaceous related disorders and due to lack of efficacy of single compounds physicians are compelled to use combined treatments (Krowchuk DP. Treating Acne—A practical guide. Medical Clinics of North America, 2000;84) from the list mentioned beneath.

Some of the ingredients useful in said treatments are categorized hereinafter by their postulated mode of action. However, it is to be understood that in some instances these ingredients operate via more than one mode of action.

Therefore, the following classifications are made herein for the sake of convenience only and are given by way of example and do not limit the ingredients to the particular application or applications indicated:

a. Topical antimicrobials such as clindamycin, tetracycline, erythromycin—having low efficacy;
b. Antimicrobials systemic class such as minocycline, clindamycin, cephalosporin, sulfur-trimethoprim—causing drug rashes and antibiotic resistance;
c. Antimicrobial and radical free generating benzoyl peroxide having low efficacy;
d. Mild steroids (in severe cases applied by way of intralesional injection)—suitable for short term treatment only, but aggravating Acne on prolonged use;
e. Classical undefined topicals such as sulfur, zinc, resorcin, salicylic acid—having low efficacy;
f. Astringents such as aluminum chloride, resorcin—inefficient and causing pruritus;
g. Topical retinoids such as natural and/or synthetic analogs of Vitamin A or retinol-like compounds which possess the biological activity of Vitamin A in the skin as well as the geometric isomers and stereoisomers of these compounds—causing photosensitivity, are slow acting and irritating;
h. Systemic (isotretinoin) retinoids—drugs with high cost, relatively high efficacy, having numerous side effects such as 100% dryness, 90% photosensitivity, 30% hair loss, 15% musculo-skeletal pains, 5% liver function disorder, and lately reported depression induction and teratogenicity;
i. Contraceptives—having all known side effects, from hyperlipidemia to pulmonary emboli, and are slow acting (require months of use);
j. Others: azelaic acid—having low efficacy; and
k. Plant extracts—scientifically non-defined as active.

A mild clinical case of Acne Vulgaris or Folliculitis is usually treated at the start by two different topicals, such as an anti-microbial and benzoyl peroxide. Mild steroids might be added. A subject suffering from a moderate condition may need the addition of a systemic antibiotic, with its obvious side effects. Topical retinoids may be added alternatively. Severe causes are generally treated by the oral isotretinoin. Due to the reluctance of the disease and to patients—derived pressures, some of the physicians are compelled to prescribe high side effect oral isotretinoin (35% incidence of severe side effects; Strauss J S et al, J Am Acad Dermatol, 2001; 45:196-207) even in patients suffering from a mild Acne Vulgaris.

There thus remains a need to provide improved topical compositions for treating inflammatory pilosebaceous disorders. There is a particular need to provide compositions and methods useful against lesions of Acne Vulgaris and of Folliculitis which:
  (i) Improve rapidly the pilosebaceous inflammation;
  (ii) Can be used topically or systemically;
  (iii) Are available to women without causing teratogenicity; and
  (iv) Are devoid of oral antibiotic or retinoid side effects.

Aluminum fluoride (Aluminum Trifluoride; Aluminum Fluoride), CAS No 7784-18-1, EINECS No. 232-051-1, having an empirical formula of $AlF_3$, (hereinafter called "AlF") is an inorganic salt approved for use as an oral care agent, i.e. as "a cosmetic ingredient and excipient used in products to polish teeth, act as oral deodorant or provide other cosmetic effects." (International Cosmetic Ingredient Dictionary and Handbook, Wenninger et al., The Cosmetic, Toiletry and Fragrance Association 8th Edition, 2000). In addition said compound is used in ceramics, as flux in metallurgy; in aluminum manufacture, as inhibitor of fermentation; and as a catalyst in organic reactions.(Merck Index, 1996)

It has now surprisingly been found that aluminum fluoride (AlF), or chemical compounds which finally release AlF, or combinations of aluminum and fluoride salts which finally release AlF, which are applied as a topical component on inflammatory lesions of Acne Vulgaris and Folliculitis causes an improvement of the lesions. A search of the literature did not reveal any reference to AlF activity on sebocytes or to a therapeutic effect of AlF on pilosebaceous inflammation, but on the contrary to adverse effects induced, for example, by fluoride toothpastes which induce Acne Vulgaris (Arch. Dermatol. Saunders M A, 1975, 111:793).

It is the object of the present invention to provide compositions, mostly topical, for controlling inflammation of the pilosebaceous gland. It is a further object of this invention to provide methods for controlling inflammation of the pilosebaceous gland.

Because of the ability of AlF to control inflammation of the pilosebaceous gland, said compositions it should be able to be used in treating in addition to Acne Vulgaris and to Folliculitis, related skin disorders in mammalian skin and scalp, such as acne rosacea, seborrhea, impetigo or psoriasis.

The present invention thus consists in compositions for the treatment of pilosebaceous gland inflammations, comprising as active ingredient AlF (as herein defined) or chemical compounds which finally release AlF, or combinations of aluminum and fluoride salts which finally release AlF.

The composition according to the present invention suitably comprises AlF at a concentration from 0.0001-50.0%, preferably between 0.001-5%; advantageously between 0.05-1.0% by weight.

The pilosebaceous gland inflammations to be treated by the composition according the present invention are preferably Acne Vulgaris and Folliculitis.

The composition according to the present invention may comprise also additional pharmaceutically and/or cosmetically acceptable compounds and/or compositions. It is thus to be understood that all the additional compounds and/or compositions mentioned below have to be acceptable.

The active agents may be formulated into various pharmaceutically and/or cosmetically compositions, e.g. a solution, a lotion, a tonic, a shampoo, a gel, a mousse, a wax, a stick, a mask, a soap, a moisturizer, a powder, a perfume, a dye, a brilliantine an aerosol, a pomade, a cream, an ointment, a paste, a systemic capsule or tablet.

The composition according to the present invention may be topically applied as such or internally ingested within a suitable carrier, solvent, dissolvent, emulgent, extract, solutions e.g. aqueous, alcoholic, oily, suspension; microemulsion, microcapsules, vesicles, etc.

The composition according to the present invention may also be formulated as an internally ingested tablet, capsule, drops or suspension. These compositions may comprise several types of carriers including, but not limited thereto, solutions, aerosols, emulsions, gels, solids, and liposomes.

The compositions according to the present invention in particular those used for the treatment of Acne Vulgaris and of Folliculitis may thus further comprise, for example, one or more supplementary pharmaceutically and/or cosmetically active compounds capable of functioning in different ways to enhance the activity of AlF and/or to provide other antiacne or antifoliculitis advantages, as follows.

a. Topical antibiotics, e.g. clindamycin, tetracycline, erythromycin, sulfacetamide, etc.;
  b. Antibiotics administered systemically, e.g. tetracycline, minocycline, doxylin, erythromycin, clindamycin, cephalosporin, sulfur-trimethoprim, etc.;
  c. Benzoyl peroxide;
  d. Topical retinoids, e.g. tretinoic acid, adapalene, isotretinoin, etc.;
  e. Systemic retinoids, e.g. isotretinoin, etc;
  f. Steroids of all strengths, from mild (e.g. hydrocortisone) to highly potent (e.g. clobetasol propionate);
  g. Non Steroidal Anti-Inflammatories, of all classes, e.g. acetic acid derivatives, oxicams, salicylates, fenemates, pyrazoles, propionic acid derivatives, etc.;
  h. Topical eicosanoids, e.g. $PGE_2$, etc;
  i. Astringents, e.g. aluminum chloride, camphor, allantoin, resorcin, etc.;
  j. Antifungals, e.g. triazoles, metronidazole, alyllamines, etc;
  k. Estrogens, e.g. Contraceptives, etc;
  l. Antioxidants, e.g. ascorbic acid and its salts, glutathione, selenium, etc.;
  m. Compounds that promote the natural tissue production of nitric oxide e.g. precursors such as L-arginine, or compounds that directly or indirectly cause the release of nitric oxide, e.g. glyceryl tri-nitrate.
  n. Other supplementary actives in use for acne, e.g. alpha-Hydroxy acids, (such as glycolic acid and lactic acid), 5-alpha reductase inhibitors, azelaic acid, bisabolol, cetyl betaine, elemental sulfur or its derivatives, lotio calaminae, salicylic acid, resorcin, zinc, zinc oxide, etc.;
  o. Vitamins, e.g. Vitamin A, Vitamin C and its salts, tocopherol (vitamin E) and other esters of tocopherol, pyridoxine, panthenol, pantothenic acid, etc.;
  p. Anti Androgens, e.g. Spironolactone, Ciproterone acetate, 5-alpha reductase inhibitors such as finasteride, etc.;
  q. Topical Sodium-Proton inhibitors, e.g. Amiloride or its derivatives, etc;
  r. Topical Amiodarone;
  s. Plant extracts known for their therapeutic effect, e.g. aloe vera, chamomile, candelilla wax, cucumber, forsynthia, ginseng, grape seed, guggal jojoba, lavender, lemon, manjistha, nettle root, rosemary, pumpkin seed, polygonum, sage, soy, tea tree oil, thyme, witch hazel etc.;

t. Soaps, e.g. soaps containing triclosan, hexachlorophene, seed or bran oils, dermatological bars, rinsing and cleaning toners, mild skin abrasives such as aluminum oxide or polyethylene microspheres, make-ups, etc.; and u. Amino acids, e.g. arginine, tryptophan, etc.

The composition according to the present invention may be applied also as part of a physical therapy, e.g. with ultraviolet, blue light spectrum or infrared radiation, of cryotherapy, of ultrasound, etc.

The composition according to the present invention may be prepared, for example, by conventional methods as becomes apparent from the Examples given hereinafter.

The present invention also consists in the use of the composition according to the present invention in the preparation of a remedy for the treatment of humans and animals of pilosebaceous gland inflammations, in particular of Acne Vulgaris and Folliculitis.

The present invention consists also in a method for the treatment of humans and animals against pilosebaceous gland inflammations, in particular against Acne Vulgaris and Folliculitis with a composition according to the present invention.

The present invention has been described in terms of preferred embodiments, but the skilled artisan will appreciate that various alterations, substitutions, omissions, and changes may be made without departing from the scope of the present invention. The amounts of said compounds being used may be varied in accordance with the specific requirements.

The present invention will now be illustrated with reference to the following Examples and to the Figs, annexed hereto without being limited by them.

In said drawings:

FIGS. 1a, 1b and 1c show a lesion of Acne Vulgaris, wherein

Figure 2:
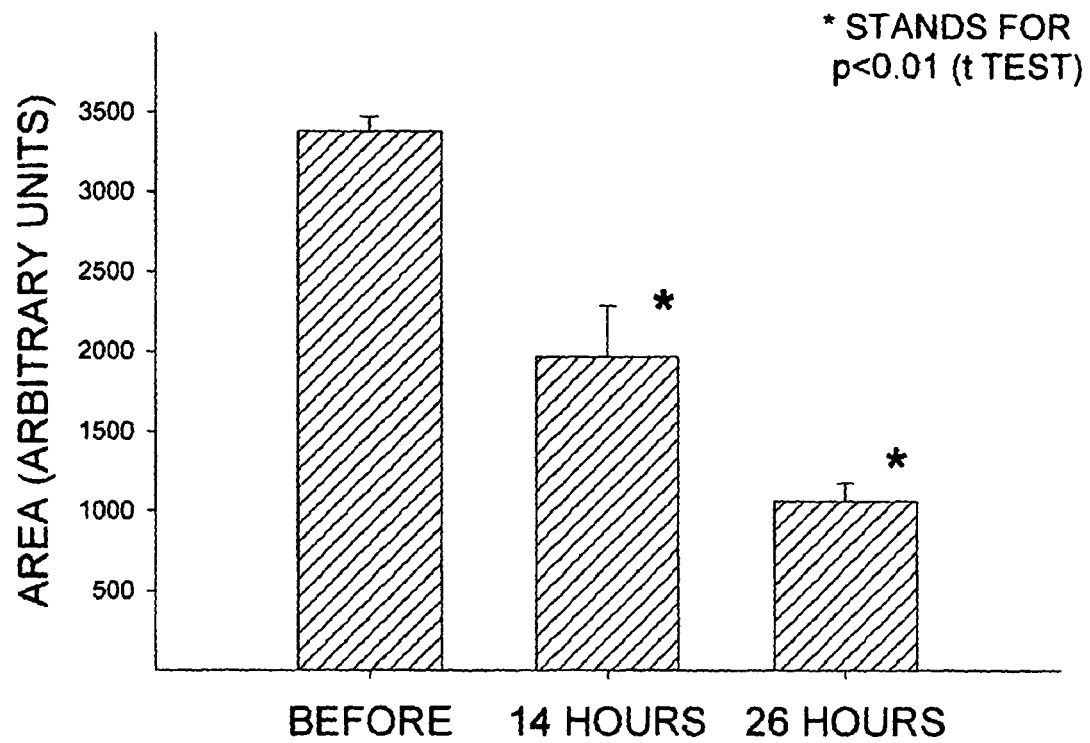
Figures 0, 3A:
Figures 3B, 10:
Figures 3C, 18:
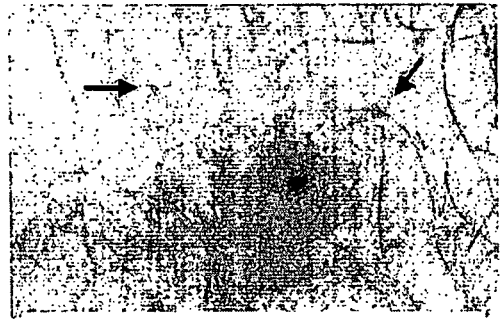
Figure 4:
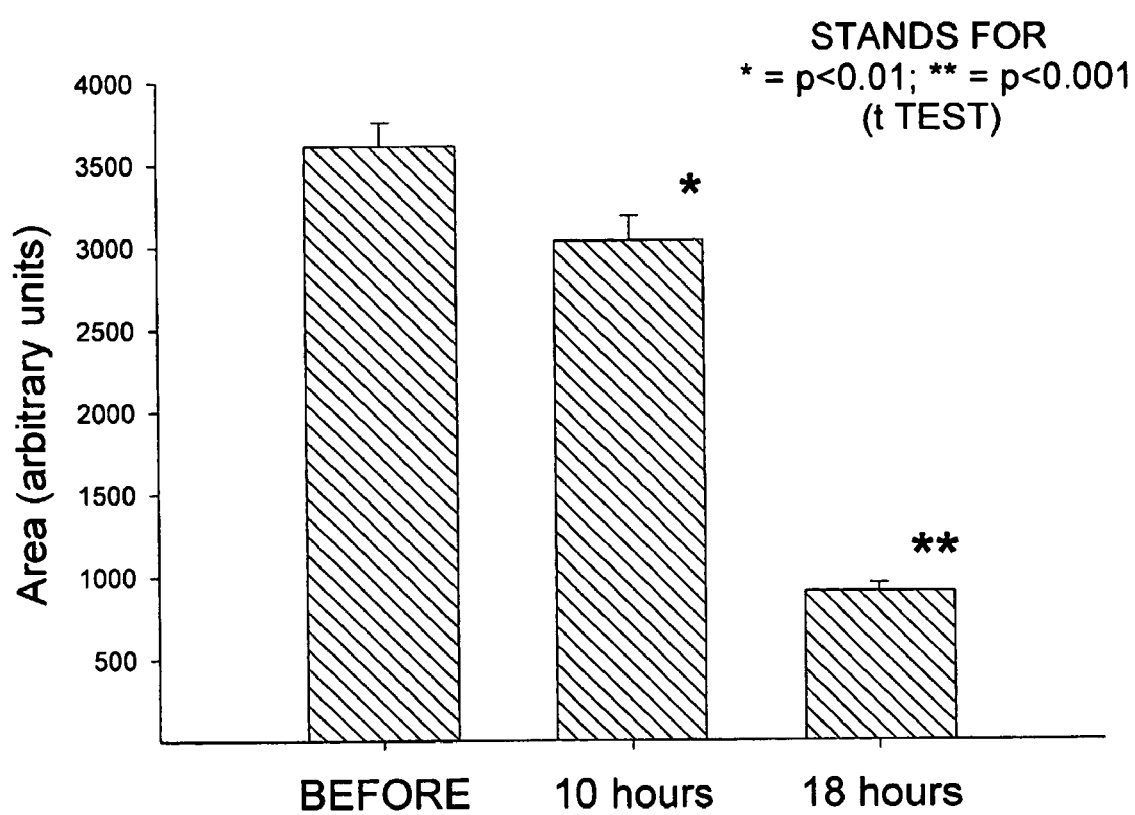
Figure 7A:
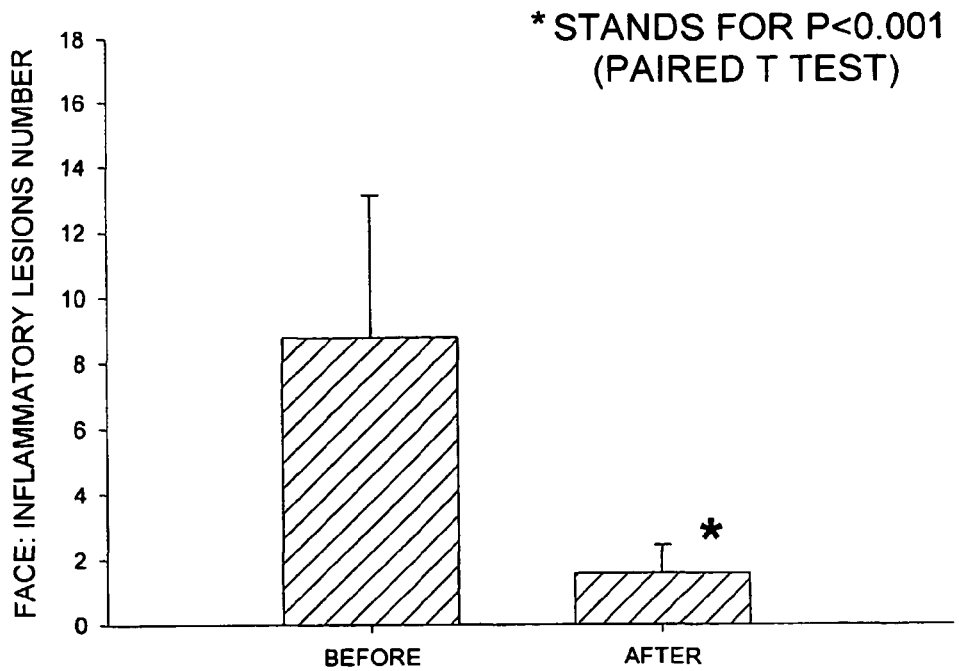
Figure 7B:
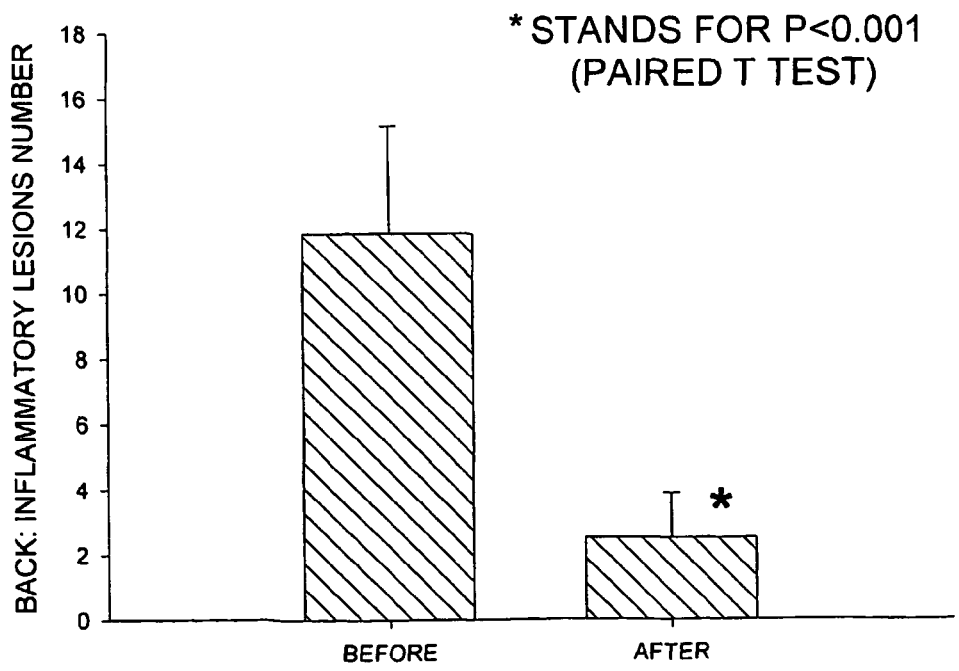

FIG. 1a shows a lesion of Acne Vulgaris after 0 hour;
FIG. 1b shows a lesion of Acne Vulgaris after 14 hour;
FIG. 1c shows a lesion of Acne Vulgaris after 26 hour;
FIG. 2 shows an Area of Lesion of Acne Vulgaris;
FIGS. 3a, 3b and 3c show a lesion of Folliculitis, wherein:
FIG. 3a shows a lesion of Folliculitis after 0 hour;
FIG. 3b shows a lesion of Folliculitis after 10 hour;
FIG. 3c shows a lesion of Folliculitis after 18 hour;
FIG. 4 shows an Area of Lesion of Folliculitis;
FIGS. 5a, 5b, 5c show subject with Severe Acne, wherein:
FIG. 5a shows subject with Severe Acne before treatment;
FIG. 5b shows subject with Severe Acne after 6 weeks from start of treatment;
FIG. 5c shows subject with Severe Acne 4 months later;
FIGS. 6a and 6b show subject with Moderate Acne, wherein:
FIG. 6a shows subject with Moderate Acne before treatment;
FIG. 6b shows subject with Moderate Acne after 3 months of treatment; and
FIGS. 7a and 7b show the counting of the number of inflammatory acne lesions, wherein
FIG. 7a shows mean number of acne lesions on the face, before and after treatment.
FIG. 7b shows mean number of acne lesions on the back, before and after treatment.

EXAMPLE 1

An Acne Vulgaris (FIGS. 1a, 1b and 1c) inflammatory lesion on the right cheek of a 12 yrs old subject was treated by AIF trihydrate at 0.5% concentration dissolved in water only. The subject applied each 3-4 h the solution as a spray. Pictures were performed in a room with artificial constant light by a Sony Mavica FD95 digital camera at a resolution of 1600×1200 pixels. The figures demonstrate rapid fading of the papule at 14 h from start of treatment and its final resolution at 26 h.

Area of inflammation was measured by image analysis techniques as follows:

Pictures (FIGS. 1a, 1b and 1c) were saved as a BMP file and loaded into Scion Imaging software v. 4.02 (NIH, USA). All three pictures were concomitantly analyzed on the same frame. First, pictures in gray scale were smoothed, manually thresholded, turned into a binary picture and the results transformed to an outline filter. The area of each outlined papule was measured by the software (n=3) and data was further plotted and statistically analyzed by student's t-test in FIG. 2 (Sigmaplot, Jandel, Java). The results (FIG. 2) demonstrate that application of AIF heals the inflamed papule within about 24 h ($p<0.01$ at 14 h and at 26 h). Any artisan in the art will recognize the surprising healing process of the papule within one day.

EXAMPLE 2

A Folliculitis (FIGS. 3a, 3b and 3c) inflammatory lesion on the left posterior thigh a 43 of a 43 yrs old subject was treated by AIF trihydrate at 0.5% concentration dissolved in water only. The subject applied each 3-4 h the solution as a spray. Pictures were performed in a room with artificial constant light by a Sony Mavica FD95 digital camera at a resolution of 1600×1200 pixels. FIGS. 3a, 3b and 3c demonstrate rapid fading of the papule at 10 h from start of treatment and its final resolution at 18 h.

Area of inflammation was measured by image analysis techniques as follows:

Pictures (FIGS. 3a, 3b and 3c) were saved as a BMP file and loaded into Scion Imaging software v. 4.02 (NIH, USA). All three pictures were concomitantly analyzed on the same frame. First, pictures in gray scale were smoothed, manually thresholded, turned into a binary picture and the results transformed to an outline filter. The area of each outlined papule was measured by the software (n=3) and data was further plotted and statistically analyzed by student's t-test in FIG. 4 (Sigmaplot, Jandel, Java). The results (FIG. 4) demonstrate that application of AIF heals the inflamed papule within about 18 h ($p<0.01$ at 10 h and $p<0.001$ at 18 h). Any artisan in the art will recognize the surprising healing process of the papule within less than one day.

EXAMPLE 3

| ANTI-ACNE CREAM o/w emulsion | |
|---|---|
| CTFA/INCI CHEMICAL NAME | % w/w |
| PART A | |
| GLYCERYL STEARATE Self-Emulsifier | 10.00 |
| PROPYLENE GLYCOL DICAPRYLATE\DICAPRATE | 8.00 |
| CETEARYL ALCOHOL and SODIUM CETEARYL SULFATE | 5.00 |
| PART B | |
| PROPYLENE GLYCOL | 3.00 |
| ALUMINUM FLUORIDE | 0.30 |
| PARABENS | 0.30 |
| PURIFIED WATER (AQUA) | 69.30 |

-continued

ANTI-ACNE CREAM o/w emulsion

| CTFA/INCI CHEMICAL NAME | % w/w |
|---|---|
| PART C | |
| SULPHUR (COLLOIDAL) | 4.00 |
| TOTAL | 100.00 |

Manufacturing procedure:
    Heat Part A and Part B, separately, at 70-75 C.°
    Add Part A on Part B under high stirring
    Cool to RT (room temperature) under moderate stirring
    Add the ingredient listed in the Part C
    Add Part C at 40 C.°

EXAMPLE 4

ANTI-ACNE CREAM w/o emulsion

| CTFA/INCI CHEMICAL NAME | % w/w |
|---|---|
| A. OIL PHASE | |
| ISOPROPYL STEARATE | 5.00 |
| PARAFFIN OIL | 15.00 |
| PRESERVATIVE | 0.20 |
| PEG-22/DODECYL GLYCOL COPOLYMER | 3.00 |
| HYDROXYOCTYL HYDROXYSTEARATE | 5.00 |
| METHOXY PEG-22/DODECYL GLYCOL COPOLYMER | 3.00 |
| B. WATER PHASE | |
| SORBITOL 70% | 5.00 |
| ALUMINUM FLUORIDE | 0.10 |
| WATER | 63.70 |
| TOTAL | 100.00 |

Manufacturing Procedure:
    Heat Part A and Part B, separately, at 75-80 C.°
    Add Part A on Part B under high stirring
    Cool to RT under moderate stirring

EXAMPLE 5

ANTI-ACNE CLEANSING GEL

| CTFA/INCI CHEMICAL NAME | % w/w |
|---|---|
| SODIUM LAUROYL SARCOSINATE | 6.70 |
| PROPYLENE GLYCOL | 8.00 |
| QUATERNIUM-15 | 0.20 |
| HYDROXYETHYLCELLULOSE | 1.00 |
| ALUMINIUM CHLORIDE HEXAHYDRATE | 2.00 |
| ALUMINUM FLUORIDE | 0.10 |
| WATER (AQUA) | 81.50 |
| PERFUME; COLOUR | 0.50 |
| TOTAL | 100.00 |

Manufacturing Procedure:
    Add Hydroxyethylcellulose in water under high stirring
    Add Quaternium-15 and mix to dissolution
    Add aluminum salts and mix to dissolution
    Add the surfactant Sodium Lauroyl Sarcosinate
    Add Propylene glycol, perfume and colour

EXAMPLE 6

ANTI-ACNE LOTION GEL

| CTFA/INCI CHEMICAL NAME | % w/w |
|---|---|
| RESORCINOL | 0.50 |
| MENTHOL | 5.00 |
| BISABOLOL | 0.20 |
| DEA-OLETH-3 PHOSPHATE | 2.50 |
| HYDROXYPROPYLCELLULOSE | 2.50 |
| AMPHOTERIC - 1 | 5.00 |
| ALUMINUM FLUORIDE | 0.10 |
| ALUMINUM CHLORIDE HEXAHYDRATE | 2.00 |
| ETHANOL 96% | 40.00 |
| WATER | 42.20 |
| TOTAL | 100.00 |

Manufacturing Procedure:
    Add Hydroxypropylcellulose in water under high stirring
    Add Amphoteric-1 and mix to dissolution
    Add aluminum salts and mix to dissolution
    Add the surfactant DEA-Oleth-3 Phosphate
    Dissolve in alcohol: Bisabolol, Menthol and Resorcinol and add to mix

EXAMPLE 7

ANTI-ACNE PEELING LOTION

| CTFA/INCI CHEMICAL NAME | % w/w |
|---|---|
| SALICYLIC ACID | 4.00 |
| ALCOHOL 96% | 17.00 |
| ALUMINUM CHLORIDE HEXAHYDRATE | 2.00 |
| ALUMINUM FLUORIDE | 0.10 |
| ROSE WATER | 76.90 |
| TOTAL | 100.00 |

Manufacturing Procedure:
    Add the aluminum salts in Rose Water
    Add and solve salicylic acid in alcohol
    Add the alcohol in water

EXAMPLE 8

ANTI-ACNE HYDROPHILIC OINTMENT

| CTFA/INCI CHEMICAL NAME | % w/w |
|---|---|
| A. Oil Phase | |
| PETROLATUM | 10.00 |
| MINERAL OIL | 10.00 |

-continued

ANTI-ACNE HYDROPHILIC OINTMENT

| CTFA/INCI CHEMICAL NAME | % w/w |
|---|---|
| CETOSTEARYL ALCOHOL | 4.00 |
| ISOSTEARYL ISOSTEARATE | 6.00 |
| B. Aqueous Phase | |
| SODIUM LAURYL SULPHATE | 1.50 |
| PURIFIED WATER (AQUA) | 38.90 |
| METHYL GLUCETH-20 | 10.00 |
| ALUMINUM FLUORIDE | 0.10 |
| C. ACTIVE INGREDIENTS | |
| PROPYLENE GLYCOL | 15.00 |
| SULFUR COLLOIDAL | 4.00 |
| PRESERVATIVE | 0.50 |
| TOTAL | 100.00 |

Manufacturing Procedure:

Heat Part A and Part B, separately, at 75-80 C.°

Add Part A on Part B under high stirring

Cool to RT under moderate stirring

At 45 C.° add the mix of Part C

EXAMPLE 9

ANTI-ACNE DAY CREAM

| CTFA/INCI CHEMICAL NAME | % w/w |
|---|---|
| A. OIL PHASE | |
| ARACHIDYL and BEHENYL ALCOHOL/ ARACHIDYLGLUCOSIDE | 2.00 |
| CETEARYL ALCOHOL and CETEARYL GLUCOSIDE | 2.00 |
| PROPYLENE GLYCOL DICAPRYLATE/CAPRATE | 8.00 |
| OCTYL ISOSTEARATE | 6.00 |
| PROPYL PARABEN | 0.20 |
| B. AQUEOUS PHASE | |
| ALUMINUM FLUORIDE | 0.30 |
| CALCIUM LACTATE | 0.25 |
| PURIFIED WATER (AQUA) | 74.05 |
| POLYACRYLAMIDE and C13-14 ISOPARAFFIN and LAURETH-7 | 0.70 |
| C. ADDITIONAL COMPONENTS | |
| CLINDAMYCIN | 0.50 |
| PRESERVATIVE | 0.50 |
| PROPYLENE GLYCOL | 5.00 |
| FRAGRANCE | 0.50 |
| TOTAL | 100.00 |

Manufacturing Procedure:

Heat Part A and B, separately to 60-65 C.°

Add the Part A to Part B and homogenize vigorously

Stir under cooling to RT

Mix together the component of Part C

Add Part C at 40 C.°

EXAMPLE 10

ANTI-ACNE NIGHT CREAM

| CTFA/INCI CHEMICAL NAME | % w/w |
|---|---|
| A. OIL PHASE | |
| ARACHIDYL/BEHENYL ALCOHOL and ARACHIDYLGLUCOSIDE | 2.00 |
| CETEARYL ALCOHOL | 2.00 |
| ISOSTEARYL ISOSTEARATE | 4.00 |
| ISOPROPYL MYRISTATE | 4.00 |
| LANOLIN ALCOHOL | 0.50 |
| STEARETH-2 | 1.20 |
| DIMETHICONE | 1.00 |
| B. AQUEOUS PHASE | |
| PURIFIED WATER (AQUA) | 70.80 |
| STEARETH-20 | 0.30 |
| ALUMINUM CHLORIDE HEXAHYDRATE | 2.00 |
| ALUMINUM FLUORIDE | 0.20 |
| COLLOIDAL SULFUR | 4.00 |
| C. ADDITIONAL COMPONENTS | |
| PRESERVATIVE | 0.50 |
| SALICYLIC ACID | 2.00 |
| FRAGRANCE | 0.50 |
| PROPYLENE GLYCOL | 5.00 |
| TOTAL | 100.00 |

Manufacturing Procedure:

Heat Part A and B, separately to 60-65 C.°

Add the Part A to Part B and homogenize vigorously

Stir under cooling to RT

Mix together the component of Part C

Add Part C at 40 C.°

EXAMPLE 11

A 22 years old woman with severe cystic acne was treated for 12 weeks with aluminum fluoride cream at 0.20 g % concentration, in a cream containing sulfur, resorcinol and clindamycin. In the past, she did not respond to classical topicals, such as benzoyl peroxide, antimicrobials and topical retinoids or to systemic antibiotic treatment. The subject applied the cream thrice daily for the first 6 weeks and twice daily afterwards. Results are shown in the enclosed FIGS. 5a, 5b and 5c and demonstrate gradual and complete disappearance of lesions after 4 months of treatment. It is obvious for a skilled artisan in the acne treatments that the results are beyond any improvement a common topical can achieve.

EXAMPLE 12

A 15 yrs old student, with mild acne, and previous antimicrobials and benzoyl peroxide treatment. The subject was instructed to apply twice daily a 0.15 g % of an aluminum fluoride cream with sulfur and resorcin. Results are shown in enclosed FIGS. 6a, and 6b and demonstrate gradual and complete disappearance of lesions after 3 months of treatment.

EXAMPLE 13

Subjects suffering from mild to severe Acne Vulgaris were treated with an anti acne cream containing aluminum fluoride at 0.5% with sulfur, resorcinol and clindamycin. Most of the patients were previously treated with either topical antiobiotics, benzoyl peroxide and/or systemic teracyclines. No other antiacne drugs were used during the treatment period. Each subject applied the cream twice daily for 4-8 weeks. Subjects were photoed before and after treatment with a Sony Mavica FD95 digital camera at a resolution of 1600×1200 pixels.

Inflammatory lesions were counted on the face (forehead or cheek, n=14 subjects, upper figure) and back (n=6 subjects, lower figure). Comparison between mean number of lesions pre and post treatment are shown in enclosed FIGS. 7a and 7b and demonstrate unprecedented accelerated disappearance of inflammatory lesions at 4 weeks from start of treatment, already. The mean number of lesions decreased from 8.8 4 to 1.6 0.9 on one aspect of the face (p<0.001, paired t test) and from 11.8 3.3 to 2.5 1.4 on back (p<0.001, paired t test).

Articles:
1. Budavary S, Ed., Merck & CO, The Merck Index, an encyclopedia of chemicals, drugs and biologicals,. Inc., 12$^{th}$ Edition, 1996.
2. Epstein E. Arch Dermatol. Fluoride toothpastes as a cause of acne-like eruptions. 1976 July; 112(7):1033-4
3. Fitzpatrick T B, Eisen A Z, Wolff K et al, Eds., Dermatology in internal medicine. Mc-Graw-Hill, In., 4$^{th}$ Edition, 1993.
4. Krowchuk D P. Treating Acne—A practical guide. Medical Clinics of North America, 2000;84:811-28.
5. Saunders M A Arch Dermatol. 1975; 111:793 Fluoride toothpastes: a cause of acne—like eruptions.
6. Taylor E J, Ed. Dorland's Illustrated Medical Dictionary, WB Saunders Comp., 27$^{th}$ Edition, 1988
7. Strauss J S et al, Safety of a new micronized formulation of isotretinoin in patients with severe recalcitrant nodular acne. J Am Acad Dermatol, 2001; 45:196-207.
8. Wenninger J A, Canterbery R C and McEwen G N, Eds., International Cosmetic Ingredient Dictionary and Handbook, The Cosmetic, Toiletry and Fragrance Association, 8$^{th}$ Edition, 2000.

The invention claimed is:

1. A composition for the treatment of acne vulgaris and folliculitis, comprising as an active ingredient aluminum fluoride or combinations of aluminum and fluoride salts which finally release aluminum fluoride, elemental sulfur and resorcin, and wherein said aluminum fluoride is present in a concentration from about 0.001% to about 1% by weight.

2. The composition according to claim 1, further comprising a pharmaceutically and/or cosmetically acceptable compound.

3. The composition according to claim 2, comprising one or more pharmaceutically and/or cosmetically acceptable active compounds selected from the group consisting of:
   a. topical antibiotics;
   b. astringents;
   c. benzoyl peroxide;
   d. topical retinoids;
   e. 5-alpha reductase inhibitors, azelaic acid, bisabolol, cetyl betaine, lotion calaminae, salicylic acid, zinc, zinc oxide;
   f. steroids;
   g. non Steroidal Anti-Inflammatories;
   h. topical eicosanoids;
   i. plant extracts known for their therapeutic effect and selected from the group consisting of, aloe vera, chamomile, candelilla wax, cucumber, forsynthia, ginseng, grape seed, guggal jojoba, lavender, lemon, manjistha, nettle root, rosemary, pumpkin seed, polygonum, sage, soy, tea tree, oil thyme, and witch hazel;
   j. antifungals;
   k. estrogens;
   l. antioxidants;
   m. compounds that promote the natural tissue production of nitric oxide;
   n. alpha-Hydroxy acids;
   o. topical Sodium-Proton inhibitors;
   p. topical Amiodarone;
   q. soaps; and
   r. amino acids.

4. The composition according to claim 1 wherein said composition is in the form of a solution, a lotion, a tonic, a shampoo, a gel, a mousse, a wax, a stick, a mask, a soap, a moisturizer, a powder, a perfume, a dye, a brilliantine an aerosol, a pomade, a cream, an ointment, a paste, a systemic capsule or tablet.

5. The composition according to claim 1 further comprising a pharmaceutical composition.

6. The composition according to claim 1 further comprising a cosmetic composition.

7. The composition of claim 1, wherein said aluminum fluoride is present in a concentration from about 0.15% to about 0.5% by weight.

8. The composition of claim 1, wherein said aluminum fluoride is present in a concentration from about 0.2 to about 0.3% by weight.

9. A method for the treatment of humans and animals against acne vulgaris and folliculitis containing administering a composition according to claim 1.

10. The method for treating humans and animals against acne vulgaris and folliculitis according to claim 9 further comprising treating said human or animal with a physical therapy selected from the group consisting of ultraviolet, blue light spectrum, infrared radiation, cryotherapy and ultrasound.

11. The method according to claim 9 wherein said composition is in the form of a solution, a lotion, a tonic, a shampoo, a gel, a mousse, a wax, a stick, a mask, a soap, a moisturizer, a powder, a perfume, a dye, a brilliantine an aerosol, a pomade, a cream, an ointment, or a paste, and wherein said administering step comprises applying said composition topically.

12. The method of claim 9, wherein said aluminum fluoride is present in a concentration from about 0.15% to about 0.5% by weight.

13. The method of claim 9, wherein said aluminum fluoride is present in a concentration from about 0.2 to about 0.3% by weight.

* * * * *